United States Patent [19]

Larsson

[11] Patent Number: 4,865,728
[45] Date of Patent: Sep. 12, 1989

[54] ADAPTOR FOR ALLOWING DIFFERENT GEL BED HEIGHTS IN A CHROMATOGRAPHIC SEPARATION COLUMN

[75] Inventor: Lars A. Larsson, Knivsta, Sweden
[73] Assignee: Pharmacia AB, Upsala, Sweden
[21] Appl. No.: 305,184
[22] Filed: Feb. 2, 1989

[30] Foreign Application Priority Data

Feb. 25, 1988 [SE] Sweden .................... 8800644

[51] Int. Cl.⁴ ........................... B01D 15/08
[52] U.S. Cl. ............... 210/198.2; 210/232; 55/386
[58] Field of Search ............. 210/198.2, 232, 236; 55/386; 422/70

[56] References Cited

U.S. PATENT DOCUMENTS

| | | | |
|---|---|---|---|
| 3,487,938 | 1/1970 | Patterson | 210/198.2 |
| 3,510,271 | 5/1970 | Emneus | 210/198.2 |
| 3,884,802 | 5/1975 | Spaans | 210/198.2 |
| 4,125,464 | 11/1978 | Burger | 210/198.2 |
| 4,228,007 | 10/1980 | Rausch | 210/198.2 |
| 4,350,595 | 9/1982 | Gunkel | 210/198.2 |
| 4,476,017 | 10/1984 | Scharff | 210/198.2 |
| 4,478,715 | 10/1984 | Goodnight | 210/198.2 |
| 4,497,711 | 2/1985 | Shephard | 210/198.2 |
| 4,549,584 | 10/1985 | Morin | 210/198.2 |
| 4,636,315 | 1/1987 | Allen | 210/198.2 |
| 4,737,284 | 4/1988 | Hauke | 210/198.2 |
| 4,737,292 | 4/1988 | Ritacco | 210/198.2 |
| 4,758,340 | 7/1988 | Marchand | 210/198.2 |

FOREIGN PATENT DOCUMENTS 3000475  7/1980  Fed. Rep. of Germany ... 210/198.2

Primary Examiner—Ernest G. Therkorn
Attorney, Agent, or Firm—Fred Philpitt

[57] ABSTRACT

To allow different gel bed heights in a chromatographic separation column (1), a plunger (6) is displaceable within the column (1) into contact with the gel bed (5) by means of a shaft (7) extending through an end piece (3) at the end of the column (1), said end piece (3) having a locking means for locking the shaft (7). According to the invention said locking means comprises a resiliently biassed locking piece (8) having grooves extending essentially perpendicular to the longitudinal direction of the shaft (7) which grooves engage corresponding grooves on the shaft (7) in the normal position of the locking piece (8). In its normal positon, the locking piece (8) is adapted to allow displacement of the shaft (7) only towards the gel bed (5). Moreover, the locking piece (8) is manually operable from its normal position to allow free displacement of the shaft (7).

2 Claims, 1 Drawing Sheet

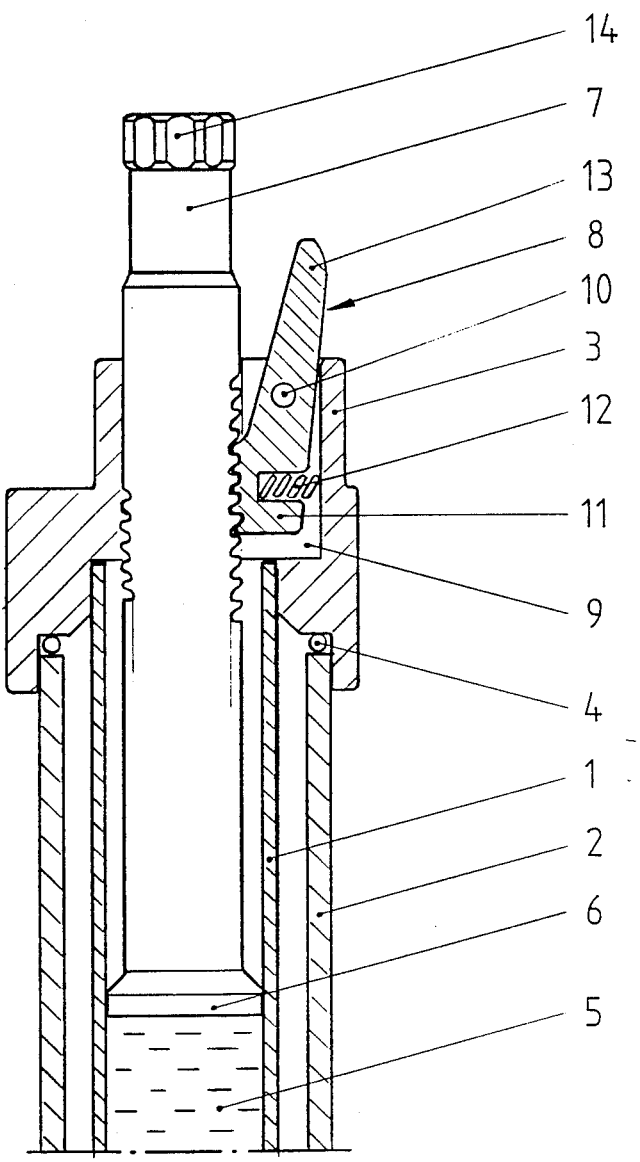

ADAPTOR FOR ALLOWING DIFFERENT GEL BED HEIGHTS IN A CHROMATOGRAPHIC SEPARATION COLUMN

The invention relates to an adaptor for allowing different gel bed heights in a chromatographic separation column, comprising a plunger which is displaceale within the column into contact with the gel bed by means of a shaft extending through an end piece at the end of the column, said end piece having a locking emans for locking the shaft. As a locking means it is known to use a screw which extends radially towards the shaft through the end piece. In this case, the shaft is locked by the friction between the end of the screw and the shaft.

However, in columns intended for high pressures such a locking has not been sufficient. In such columns the plunger is exposed to great axial forces which can cause a displacement of the plunger from its set position. This in turn leads to the formation of an undesirable interspace between the plunger and the gel bed.

At very large columns it is also known to have a threaded shaft by means of which the plunger can be screwed towards the gel bed through a nut provided in the end piece. However, this is a very time-consuming procedure.

The object of the invention is to bring about an adaptoro which in a quick and simple manner enables a secure setting of the plunger against the gel bed.

This is attained in that the locking means comprises a resiliently biased locking piece having grooves extending essentially perpendicular to the longitudinal direction of the shaft, said grooves engaging corresponding grooves on the shaft in the normal position of the locking piece, said locking piece, in its normal position, being adapted to allow displacement of the shaft only towards the gel bed, and said locking piece being manually operable from its normal position to allow free displacement of the shaft.

BRIEF DESCRIPTION OF THE DRAWING

The invention will be described more in detail below with reference to the attached drawing on which the single FIGURE shows a longitudinal section of one end of a separation column provided with an embodiment of an adaptor according to the invention.

DESCRIPTION OF THE PREFERRED EMBODIMENTS

A separation column of a type known per se, is denoted 1. In the embodiment shown, the separation column 1 is surrounded by a cooling jacket 2 to enable a cooling medium, e.g. water, to be fed to and from the interspace between the column 1 and the jacket 2 in a manner not shown. The end of the column 1 is received in an end piece 3 which is supposed to be screwed onto the jacket. An O-ring 4 is placed between the upper end of the jacket 2 and the end piece 3 to seal the jacket 2 and the end piece 3.

The column 1 is supposed to be filled to a certain level with a separation gel bed 5. The gel bed 5 is kept in place in the column 1 by means of a plunger 6 which is displaceable in the column 1 into contact with the gel bed 5 by means of a shaft which extends through a center hole in the end piece 3.

In a manner known per se the plunger 6 comprises sealing means (not shown) for sealing against the inside of the column 1 as well as a support filter (not showon) for the gel bed 5.

In a manner known per se supply means (not shown) extends through the shaft 7 for supplying a sample to be separated to the gel bed 5.

To lock the shaft 7 with the plunger 6 in contact with the gel bed 5, the end piece 3 comprises a lever-shaped locking piece 8 in a recess 9.

In the embodiment shown, the locking piece 8 is pivoted on a pin 10 extending perpendicular to the longitudinal axis of the shaft 7 within the recess 9.

One arm 11 of the locking piece 8 is provided with threads on a segment facing the shaft 7. By means of a compression sprg 12 inserted between the arm 11 and the wall of the recess 9 these threads are in engagement with corresponding threads on the shaft 7 in the normal position of the locking piece 8 as shown on the drawing.

In the embodiment shown the other arm 13 of the locking piece 8 abuts the wall of the recess 9 with a portion facing away from the shaft 7.

Thus, in the normal position of the locking piece 8 as shown on the drawing the shaft 7 with the plunger 6 can manually be displaced towards the gel bed 5 against the action of the compression sprg 12 to quickly and coarsely adjust the position of the plunger 6. To finely adjust the position of the plunger 6 the shaft 7 can, then, be screwed into tight contact with the gel bed 5 by means of a grooved flange 14 at the free end of the shaft 7.

By manually bringing the arm 13 of the locking piece 8 towards the shaft 7, the threads of the arm 11 are brought out of engagement with the threads on the shaft 7 whereby the shaft 7 can be freely displaced in the end piece 3.

Of course, it is not necessary that the engagement between the arm 11 of the locking piece 8 and the shaft 7 takes place via threads but the engagement can instead take place via grooves in case one does not want to be able to finely adjust the position of the plunger 6 in the column 1.

As an alternative to the lever-shaped locking piece 8, any kind of a resiliently biassed locking piece is possible as long as it in its normal position allows displacement of the shaft 7 only towards the gel bed 5. As an example, a push button operated locking piece can be mentioned, which in one of its positions is in engagement with the shaft 7 and which in its other position is out of engagement with the shaft 7. Other embodiments of the locking piece should be apparent to anyone skilled in the art.

Thus, a quick, a simple and exact adjustment of the plunger 6 relative to the gel bed 5 is made possible by means of the adaptor according to the invention. Also, the plunger may quickly and simply be removed from the gel bed 5 by pulling out the shaft 7 after that the arm 13 of the locking piece has been pressed towards the shaft 7.

I claim:

1. Adaptor for allowing different gel bed heights in a chromatographic separation column (1) comprising a plunger (6) which is displaceable within the column (1) into contact with the gel bed (5) by means of a shaft (7) extending rhough an end pice (3) at the end of the column (1), said end pice (3) having al ocking means for locking the shaft (7), characterized in that said locking means comprises a resiliently biassed locking piece (8) having grooves extending essentially perpendicular to the longitudinal directin of the shaft (7), said grooves engaging corresponding grooves on teh shaft (7) in the normal position of the locking piece (8), said locking piece (8), in its normal position, being adapted to allow displacement of the shaft (7) only towards the gel bed (5), and said locking piece (8) being manually operable from its normal position to allow free displacement of the shaft (7).

2. Adaptor according to claim 1, characterized in that the grooves on both the locking piece (8) and the shaft (7) are threads for enabling fine adjustment of the plunger (6) relative to the gel bed (5) by turning the shaft (7) in the end piece (3).

* * * * *